United States Patent [19]

Benedyk

[11] Patent Number: 4,962,039

[45] Date of Patent: Oct. 9, 1990

[54] SIMPLE AND RAPID METHOD FOR DETECTING THE PRESENCE OF WATER IN VARIOUS ORGANIC FLUIDS

[75] Inventor: Donald T. Benedyk, Brighton, Mich.

[73] Assignee: 2V Industries, Inc., Wixom, Mich.

[21] Appl. No.: 214,016

[22] Filed: Jun. 30, 1988

[51] Int. Cl.$^5$ .................. C09C 3/00; G01N 33/18
[52] U.S. Cl. ............................ 436/40; 436/39; 436/60; 436/164
[58] Field of Search .................. 436/40, 39, 60, 164

[56] References Cited

U.S. PATENT DOCUMENTS

| | | | |
|---|---|---|---|
| 2,950,958 | 8/1960 | Nesh | 436/40 |
| 4,257,775 | 3/1981 | Ladov et al. | 436/40 |
| 4,578,357 | 3/1986 | Melpolder | 436/40 |
| 4,699,885 | 10/1987 | Melpolder | 436/40 |

FOREIGN PATENT DOCUMENTS 2906773  8/1980  Fed. Rep. of Germany.

*Primary Examiner*—Robert J. Warden
*Assistant Examiner*—Lynn M. Kummert
*Attorney, Agent, or Firm*—Basile and Hanlon

[57] ABSTRACT

A method for determining the presence of water in an organic test fluid including the steps of admixing a portion of the organic test fluid with a liquid indicator system containing a non-polar solvent which is soluble in the organic test fluid, and comprises a petroleum distillate. The solvent also includes a non-hazardous water soluble dye which will evidence a color change upon direct contact with water. The mixture is agitated to permit intimate contact between the indicator system and the organic test fluid. The mixture is then allowed to stand for a period in which the dye will react with any water contained in the organic test fluid, and provide a color indication thereof.

10 Claims, No Drawings

SIMPLE AND RAPID METHOD FOR DETECTING THE PRESENCE OF WATER IN VARIOUS ORGANIC FLUIDS

BACKGROUND OF THE INVENTION

1. Field of the Invention

This invention relates to a method for accurately determining the presence or absence of water in low concentration levels in organic fluids and an indicator system which can be employed in this method. More particularly this invention relates to a method for determining the presence or absence of water in non-polar organic fluids such as petroleum oil or hydrocarbon oils which can be performed rapidly without costly instrumentation and tedious and time consuming analytical methods.

2. Description of the Relevant Art

Determination of the presence or absence of water in various organic fluids is quite important. In materials such as transmission fluid, the presence of water at elevated levels has been found to have deleterious affects on mechanical devices using organic fluids such as transmission brake devices, hydraulic devices, etc. Strict tolerances about the absence of water in organic fluids can be seen in other areas as hydraulic oils and petroleum fuel.

Because of this, variety of analytical methods have been developed to determine the water content in organic materials. The classic method for the determination of water is the Karl Fischer method. This method relies on the stoichiometric reaction of water with Karl Fisher reagent, a mixture of pyridine, iodine, sulphur dioxide and methanol. Addition of Karl Fischer reagent to a sample containing water will result in a color change from light yellow in the presence of excess water, to dark brown in the presence of excess Karl Fischer reagent signifying a drop in electrical resistance as the water reacts with reagent. Titration to a specific consistent electro-resistive end point can be used to calculate the water content of a given organic material.

The Karl Fischer method is an accepted and accurate method for water content determination. However, it does have drawbacks. First, the method is time consuming and requires a degree of skill and training to provide accurate results. The apparatus is complex; requiring a meter electrode, numerous drying tubes, agitation means, etc. which must be air-tight in order to function accurately. Second, the method is unable to provide a high degree of accuracy for samples containing smaller amounts of water or various alcohols. Water concentration as low as 0.04% is extremely difficult to accurately detect. However, water level in a given sample below the accurate detection limits of the method can still be sufficient to create problems in the given application. Third, the Karl Fischer reagent, at the least is, unpleasant to work with. The reagent has a relatively short shelf life and can be expensive if large quantities are required. Finally, the reddish brown color of the reagent makes it extremely difficult to titrate red and brown colored samples accurately.

Numerous attempts have been made to modify the Karl Fischer reagent to produce a more cost effective reagent which would yield accurate results at lower water concentrations. These attempts have not produced a quick and reliable method which can be used easily to analyze water content in a variety of fluids or in a field test environment.

A second water determination method which is widely used is the Standard Test Method for Water in Petroleum Products and Bituminous Materials by Distillation (ASTM D 95-70) which is herein incorporated by reference. The material to be tested is heated under reflux with a water immiscible solvent which co-distills with the water in the sample. Condensed solvent and water are continuously separated in a trap with the water settling in a graduated section of the trap while the solvent is returned to the still.

The distillation method is effective for samples containing concentrations of water above approximately 0.5 to 1%. The accuracy decreases as the concentration of water decreases. Thus, the method is not desirable for trace analysis. Distillation by this method is an extremely slow procedure. Accurate determination can take up to an hour or more per sample. This is impractical where large number of samples must be run or there is extreme urgency, as is the case in many situations. As with the Karl Fischer method, supervision of test method by technically trained personnel is highly desirable to maintain accuracy and reproducability.

Other methods such as infrared spectroscopy (IR) and ultracentrafugation are used in certain circumstances. Infrared spectroscopy requires expensive instrumentation operated by experienced analysts as well as careful sample preparation and the use of special IR cells. Ultracentrafugation is not a reliable method for determining water content in highly emulsified samples.

Thus, there has been a great need to develop rapid, accurate, easy, cost-effective method for determining water content in non-polar materials. Despite this ease, accuracy, speed and economy have been elusive goals.

A variety of field test methods for determining the presence of water in organic fluids have been proposed. These methods and devices have resulted in some simplification. However, the methods still have drawbacks.

U.S. Pat. No. 4,577,978 to Pullen et al, discloses a field method for determining small amounts of water in industrial and lubricating oils. A measured amount of test oil is heated in a first self-contained compartment simultaneously with the heating of a reference oil containing a known quantity of water in a second compartment. The operator observes the bubbles generated upon heating to provide a relative indication of the water content in the sample. The test takes about five minutes, but provides only transient evidence of water content. Great reliance must be placed on the operator's power of observation, skill, and reliability. Additionally, this method would not be as effective for oils containing low boiling components.

An aircraft fuel contaminant test unit is discussed in U.S. Pat. No. 3,976,572 to Reick. The device has two chambers connected by a selectively permeable hydrophobic material constructed from non-woven spunbonded polyester or polyethylene fibers. The polymeric fibers are coated with a hydrophobic material which includes fumed silicon dioxide particles. This visual testing device would be effective for gross quantities of water but is not designed for detecting trace amounts. Additionally, the device would be difficult to use successfully to test highly viscous materials. A method for determining the presence minute traces of water in organic liquids was proposed in U.S. Pat. No. 2,950,958 to Nesh. The organic liquid to be tested is mixed with anhydrous carbon tetrachloride and agitated to extract the water molecules from solution. Powdered methylene blue is added to the agitated mixture. Any water released from the liquid material will dissolve the methylene blue triggering a color change.

The drawbacks to the Nesh method are numerous. First, the multi step system in which indicator is added after extraction is cumbersome, time-consuming, and inaccurate. Second, the use of carbon tetrachloride is considered to be unsafe. Third, it is doubtful that the detection levels obtainable by the Nesh method are as sensitive as would be desirable. This may be the reason this method has failed to attain wide acceptance. Finally, it is not believed that this method would be completely effective on pigmented or colored samples.

Thus, it would be desirable to provide a method for detecting water in non-polar materials which is rapid, precise, easy to use, and cost effective and which eliminates the need for complex instrumentation and sample preparation by highly skilled personnel.

It is also desirable to provide an indicator system which can be used to detect the presence of varying amounts of water in a variety of opaque, pigmented or clear liquid samples.

Finally, it is desirable to provide a method and an indicator system which can be used by individuals with little or no technical training and still achieve accurate results.

SUMMARY OF THE INVENTION

The present invention is a method for detecting the presence of water in various organic fluids and an indicator system which can be employed in this method. The detection method includes the following steps:

A. contacting a portion of the organic fluid to be tested with a measured amount of an indicator system, the indicator system comprising a non-hazardous water-soluble dye contained in a non-polar solvent;

B. agitating the combined mixture for a period sufficient to permit intimate contact between the indicator and the organic fluid to be tested; and C. allowing the agitated mixture to set for a period sufficient to permit the dye to react with water contained in the test fluid and yield a visually discernable indication of water content therein.

The indicator system of the present invention is suitable for detecting trace amounts of water in a variety of organic fluids. The system is composed of an anhydrous non-polar solvent which is essentially immiscible in water and a water-soluble dye present in the solvent in a concentration between about 0.001% and about 0.1%.

DESCRIPTION OF THE PREFERRED EMBODIMENTS

The present invention is based upon the unexpected discovery that a dry, powdered, water-soluble dye, when suspended in a suitable non-polar solvent, will function as a sensitive and accurate indicator of trace amounts of water in organic fluids such as transmission fluid, hydraulic oils and the like. The water levels at which detection is possible are surprisingly lower than that previously obtainable by known conventional methods. In addition, the indicator system permits the detection of water in a variety colored or pigmented materials in which detection would have previously been impossible.

The present invention is directed to a method for detecting the presence of water in an organic fluid. The organic fluids which can be successfully analyzed include those generally having a viscosity less than 5000 SUS and a color intensity less than 16 on the Gardner scale. Suitable materials include fluids for which it was heretofore extremely difficult to obtain accurate water content analysis. Example of these include automatic transmission fluid, cutting oil, and hydraulic fluid and the like. Other fluids suitable will be readily known to one reasonably skilled in the art upon reading this disclosure.

In the method of the present invention, a measured portion of the organic fluid to be analyzed is dispensed into a suitable analytical container such as a cell. The amount of fluid employed depends upon the characteristics of the test sample, such as viscosity, color intensity and suspected water content. In the preferred embodiment, a portion of test sample in an amount between about 1 ml and 100 ml is employed.

Into this measured portion of the test sample, there is introduced a measured portion of a specified indicator system. The material is then agitated and the presence of water is visually indicated after a specified reaction period which will be described in detail subsequently.

The indicator system of the present invention comprises a non-polar solvent soluble in the organic fluid to be tested and a powdered, water-soluble dye suspended therein.

The non-polar solvent successfully employed in this invention is a petroleum distillate which is essentially immiscible in water and has a viscosity less then about 200 SUS. Without being bound by any theory, it is believed that low viscosity maximizes contact between the water in the sample and the dye material.

The non-polar solvent selected will generally be incapable of absorbing significant amounts of water from the atmosphere. This can be due either to its inherent general non-reactivity with water or elevated vapor pressure. The non-polar solvent is selected from the group consisting of aromatic compounds such as mineral seal oil, mineral spirits, kerosene fraction cuts and mixtures thereof. The preferred kerosene fractions are those having a boiling point between about 180° and about 300° C. and a flash point between about 100° and about 150° F.

The dye material chosen is water soluble and evidences a color change upon contact with water. Preferably, the dye employed is admixed in powder form with the chosen non-polar solvent where it will remain essentially undissolved until contacting water contaminants contained in the test sample. Ideally, the dye is essentially colorless while suspended in the non-polar solvent but will yield a vivid color either by reaction or simple dissolution when brought into contact with water in the sample. In the preferred embodiment, dye distributed under the tradename "ACID BLUE #9" is employed. This material is commercially available can be obtained through distributors such as ChemCentral in Detroit, Mich.

Other suitable dyes include:

Acid Blue 9, Acid Blue 1, Acid Blue 25, Acid Blue 45, Direct Blue 86, FD and C Blue 1, Basic Blue 7, Acid Red 73, Acid Red 52, Acid Red 14, Acid Yellow 73, Acid Yellow 17, Acid Yellow 23, Acid Green 1 and suitable mixtures thereof.

It has been found unexpectedly that there is a direct relationship between variations in the concentration of the dye contained in the solvent and the sensitivity level of the dye to various concentrations of water contained in the sample. The amount of dye necessary to indicate a specific concentration of water will vary from dye to dye depending on the chemical properties of the dye. When ACID BLUE #9 is employed, it has been found that the presence of water can be detected with as little as 0.044 mg dye suspended in 5 ml of solvent admixed with an equal volume of test sample. Higher concentrations of dye can be used to indicate the presence of lower concentrations of water. In the preferred embodiment, it has been found that 0.1 mg of ACID BLUE #9 carried in 5 ml of suitable solvent will provide an indication of water at concentrations of 0.08% when admixed with 5 ml of conventional transmission fluid according to the method of the present invention. Water concentration levels as low as 0.02% can be obtained when amounts of ACID BLUE #9 equalling about 0.3 mg are used. Thus, in the preferred embodiment, the amount of ACID BLUE #9 dye present in each 5 ml portion of solvent is between about 0.044 mg and about 0.3 mg. It is to be understood that other dyes having differing reactivities may require slightly different concentrations to achieve equivalent effectiveness. Such variation are considered as a part of this invention.

The type and color of water-soluble powdered dye employed will, generally, depend upon the type of organic fluid to be analyzed. It has been found that blue dyes are most effective for a wide variety of colored or colorless organic fluids. Blue dyes provide a dramatic color change even in samples containing red pigmentation such as various lubricating oils. However, where desired, various colored dyes can be employed within the scope and teaching of this disclosure.

The concentration of dye can be calibrated to provide a color gradient to permit reasonably accurate approximation of water content. Alternately the dye can be present in the solvent in a predetermined amount to provide a specific YES/NO test for a given concentration of water. Reference is made to the illustrative examples for one such instance of a YES/NO test.

The volume of non-polar solvent to be admixed with the test sample can vary depending on the characteristics of the test sample. Samples having intense colors, high viscosities or relatively high water concentrations will generally require larger volumes of non-polar solvent to permit accurate readings. Without being bound to any theory, it is believed that this is due to several factors. Where color intensity is a problem, dilution serves to reduce the color intensity thereby rendering subtle color changes more apparent. Where samples are highly viscous, dilution serves to insure intimate contact between the contained water and the dye material. In samples with relatively high water concentrations, dilution reduces the intensity of the resulting dye color making visual determination easier and more accurate.

In the preferred embodiment, approximately equal volumes of solvent to test sample have been employed. This would appear to provide great ease of measurement and accuracy for a wide variety of samples. However, given the nature of various test samples, the ratio of non-polar solvent to test sample can vary from about 3 parts solvent to about 1 part test sample to about 1 part solvent to about 9 parts test sample.

Once the test sample is combined with the non-polar solvent and indicator, the mixture is agitated for a period sufficient to provide intimate contact between the indicator and the organic fluid. This period can vary from about 30 seconds to about 5 minutes depending on the amount of non-polar solvent employed, the amount of dye employed, and nature of test fluid. In the preferred embodiment, where equal volumes of non-polar solvent and test sample of about 5 ml each are employed, the agitation interval is between about 30 seconds and 1 minute.

Once the mixture has been agitated, it is permitted to remain undisturbed for a period sufficient to permit the water contained in the sample solvent mixture to react with the water-soluble dye. The term "react" as defined herein encompasses both chemical reactions in their classic sense as well as physical reactions such as the dissolution of the water soluble dye in the contained water.

It has been found that a sitting or resting period between about 10 minutes and about 30 minutes is sufficient for making a determination of water content in most samples. In the preferred embodiment, a resting period of about 5 minutes is sufficient to permit accurate detection of water in the organic sample. In many instance resting periods as short as one to two minutes are sufficient.

It has been found that the test method of the present invention, provides an accurate and lasting indication of the test conducted. This is particularly true of the YES/NO version of this method. In the preferred embodiment, dye color will remain true for a period of at least 5 hours. This can permit independent verification of the test by other individuals in various lighting conditions.

Additionally, indicator-solvent systems produced according to the present invention are believed to have a shelf life equal to or greater than conventional Karl Fischer reagent or powdered dyes not mixed with non-polar solvents.

In order to further illustrate the present invention, reference is made to the following examples. The material contained in the following examples is to be construed as illustrative and in no way limitative of the present invention.

EXAMPLE I

The accuracy of the method of the present invention was compared to unfrared (IR) analysis and to azeotropic distillation. Samples of transmission fluid containing between 0.01% and 0.5% water were prepared.

Water determination by FTIR was performed on a Michelson FTIR. The instrument was calibrated by preparing standards containing 0.01% emulsified water in virgin transmission fluid and 0.5% emulsified water in virgin transmission fluid to prepare low and high range standards. Samples were run and percent water was calculated. The results are set forth in Table I.

Water contents of samples were also determined using the azeotropic distillation method set forth in ASTM D 95-70 which is herein incorporated by reference. The 300 ml of each sample was admixed with 500 ml reagent grade xylene and refluxed with stirring for 30 minutes at 250° F. The volume of water was collected and percent water calculated. The results of each distillation are set forth in Table I.

The same samples were analyzed using the calorimetric method of the present invention. Equal volumes of test transmission fluid and test solution were admixed for 30 seconds; yielding an initial red color. The test solution contained 25 mg of Acid Blue 9 dye in 5 ml kerosene solvent. The samples were, then, allowed to sit undisturbed for 1 to 2 minutes. Color changes from red to blue indicated the presence of water at an amount equal to or greater than 0.01%. The results are set forth in Table I.

Thus, it can be seen that the method of the present invention provides an accurate and fast means to determine the presence of water at or about 0.01%.

TABLE I

COMPARISON OF VARIOUS WATER TEST METHOD

| SAMPLE | ACTUAL WATER CONTENT (%) | WATER CONTENT (ANALYTICAL) | | TEST METHOD Positive/Negative |
|---|---|---|---|---|
| | | FTIR (%) | DISTIL-LATION (%) | |
| A | 0.01 | 0.1 | 0.02 | Positive |
| B | 0.03 | 0.08 | 0.05 | Positive |
| C | 0.08 | 0.1 | 0.18 | Positive |
| D | 0.5 | 0.56 | 0.5 | Positive |
| C | 0 | 0 | 0 | Negative |

EXAMPLE II

Samples of various lots of transmission fluid were tested using the method and indicator of the present invention. Duplicate samples were quantitatively analyzed using the azeotropic distillation method described previously. The sample sizes for azeotropic distillation were 1000 ml each. Samples sizes for colorimetric tests were 10 ml each.

The indicator solution employed in these tests was composed of Acid Blue 9 and xylene. The test procedure was the same as indicated in Example I. The results of the tests is set forth in Table II.

As can be seen from these positive results, i.e., a noticeable color change from red to blue was obtained in all samples containing over 0.038% $H_2O$.

TABLE II

DETERMINATION OF TEST METHOD SENSITIVITIES AT VARIOUS WATER CONTENT LEVELS

| SAMPLE | WATER CONTENT (%) | VISUAL RESULT FROM COLORIMETRIC TEST |
|---|---|---|
| 1 | 0.075 | Positive |
| 2 | 0.075 | Positive |
| 3 | 0.075 | Positive |
| 4 | 0 | Negative |
| 5 | 0.075 | Positive |
| 6 | 0.038 | Positive |
| 7 | 0.038 | Positive |
| 8 | 0.038 | Positive |
| 9 | 0.038 | Positive |
| 10 | 0.038 | Positive |
| 11 | 0.075 | Positive |

EXAMPLE III

The dye methylene blue described in U.S. Pat. No. 2,950,958 to Nesh was evaluated and compared to the method of the present invention.

Transmission fluid samples were prepared containing 0.08 percent water. Varying amounts of either acid blue 9 or methylene blue were admixed with 10 ml of a selected solvent; either methylene blue or acid blue 9. Five ml of transmission fluid was then added and the tube was agitated for 30 seconds. The tubes were allowed to sit undisturbed. Observations were recorded at 15 and 30 minutes.

The composition of each test solution is recorded in Table III. The results of tests are recorded in Table IV.

As can be seen from the results in Tables III and IV, the methylene blue indicator solution failed to exhibit a color change at stoichiometric concentrations as dilute as acid blue 9. Even when a response did occur, methylene blue was not as vivid as acid blue 9.

TABLE III

| SAMPLE | DYE (grams) | | SOLVENT (ml) | |
|---|---|---|---|---|
| | AB9[1] | MB[2] | Kerosene | $CCl_4$ |
| A | 5.6 | — | 10 | — |
| B | 12.3 | — | 10 | — |
| C | 18.0 | — | 10 | — |
| D | — | 9.9 | — | 10 |
| E | — | 4.1 | — | 10 |
| F | — | 15.0 | — | 10 |
| G | 10.8 | — | — | 10 |

[1] acid blue 9
[2] methylene blue

TABLE IV

| SAMPLE | 15 MINUTE OBSERVATION | 30 MINUTE OBSERVATION |
|---|---|---|
| A | Trace Violet | Light Violet |
| B | Violet | Light Blue |
| C | Strong Violet | Deep Blue |
| D | No color change | No color change |
| E | No color change | No color change |
| F | Trace Violet | Trace Violet |
| G | Strong Violet | Light Blue |

What is claimed is:

1. A method for detecting the presence of water in an organic fluid selected from the group consisting of transmission fluid, cutting oil, hydraulic fluid, and mixtures thereof comprising the steps of:

a. first, admixing a portion of the organic fluid with a measured amount of a liquid indicator system, the liquid indicator system comprising an anhydrous non-polar solvent selected from the group consisting of mineral seal oil, mineral spirits, kerosene, and mixtures thereof having a boiling point between about 180° and about 300° F. and a flash point between about 100° F. and about 150° F. in the organic fluid, and a non-hazardous water soluble dye which is essentially insoluble and colorless in the anhydrous, non-polar solvent and evidences a color change upon direct contact with water, the dye being present in an amount between about 0.044 mg. dye per 5 ml of solvent and about 0.3 mg dye per 5 ml solvent;

b. second, intimately dispersing any water contained in the organic fluid throughout the combined mixture by agitating the combined mixture for a period sufficient to provide intimate contact between the indicator system and the organic fluid; and c. third, allowing the agitated mixture to sit for a period sufficient to permit any water present in the mixture to react with the water soluble dye.

2. The method of claim 1 wherein the ratio of indicator system to organic fluid is between about one part organic fluid to three parts indicator system and about nine parts organic fluid to about one part indicator system.

3. The method of claim 1 wherein the ratio of non-polar solvent to organic fluid is about one to one.

4. The method of claim 1 wherein the dye is present in an amount between about 0.044 mg dye per 5 ml of solvent and about 0.1 mg of dye per 5 ml of solvent.

5. The method of claim 1 wherein the organic fluid has viscosity less than about 5000 SUS and a color having a Gardener value less than about 16.

6. The method of claim 1 wherein the agitation proceeds for a period between about 20 seconds and about 40 seconds.

7. The method of claim 6 wherein the agitation proceeds for a period of about 30 seconds.

8. The method of claim 1 wherein the settling period is between about 5 seconds and about 30 minutes.

9. A liquid indicator system suitable for detecting trace amounts of water in organic fluids consisting essentially of:

an anhydrous non-polar solvent selected from the group consisting of kerosene, mineral spirits, mineral seal oil and mixtures thereof which are essentially immiscible in water; and a water soluble dye present in the solvent in concentrations between about 0.001% and about 0.1%, said dye being capable of reacting in the presence of trace amounts of water to yield a colored solution, said dye selected from the group consisting of Acid Blue 9, Acid Blue 1, Acid Blue 25, Acid Blue 45, Direct Blue 86, FD and C Blue 1, Basic Blue 7, Acid Red 73, Acid Red 52, Acid Red 14, Acid Yellow 73, Acid Yellow 17, Acid Yellow 23 and Acid Green 1.

10. The indicator system of claim 9 wherein the kerosene is selected from the group having a flash point between about 100° F. and about 150° F. and a boiling point between about 180° C. and about 800° C.

* * * * *